United States Patent [19]

Fuller et al.

[11] Patent Number: 4,760,105
[45] Date of Patent: Jul. 26, 1988

[54] POLYIMIDE MODIFIED EPOXY RESINS IN AQUEOUS EMULSIONS FOR LAMINATION AND ELECTRODEPOSITION

[75] Inventors: Timothy J. Fuller, Berkeley Heights, N.J.; Joseph R. Marchetti, Hempfield Township, Westmoreland County; Zal N. Sanjana, Penn Hills Township, Allegheny County, both of Pa.

[73] Assignee: Westinghouse Electric Corp., Pittsburgh, Pa.

[21] Appl. No.: 785,812

[22] Filed: Oct. 9, 1985

[51] Int. Cl.$^4$ .................. C08G 59/62; C08G 59/46; C08G 59/44; C08L 63/00

[52] U.S. Cl. .................. 523/420; 523/414; 528/96; 528/111.3; 528/114

[58] Field of Search .................. 523/414, 420; 528/96, 528/114, 111.3

[56] References Cited

U.S. PATENT DOCUMENTS 4,130,469  12/1978  McGinnis .................. 523/414
4,384,946   5/1983  Patzschke .................. 523/414

FOREIGN PATENT DOCUMENTS 48-67394   9/1973  Japan .................. 528/114
49-97898   9/1974  Japan .................. 528/114
49-38119  10/1974  Japan .................. 528/96
49-44957  11/1974  Japan .................. 528/96

*Primary Examiner*—C. Warren Ivy
*Attorney, Agent, or Firm*—Daniel P. Cillo

[57] ABSTRACT

Disclosed in an emulsion having a discontinuous phase that consists of a water dispersed or water emulsified epoxy resin in water having at least two epoxide groups, a water soluble salt of an imide compound having at least one carboxyl group, and a crosslinking agent; the discontinuous phase has excess epoxide functionality. The continuous phase is water. A method of forming a coating on a conductive substrate is also disclosed. The substrate and an electrode are immersed into the emulsion and a direct current is applied between the substrate and the electrode to electrophoretically deposit a coating on the substrate of the epoxy resin, the imide compound, and the crosslinking agent. The substrate is removed from the emulsion and is heated to a temperature sufficient to cure the coating.

11 Claims, 1 Drawing Sheet

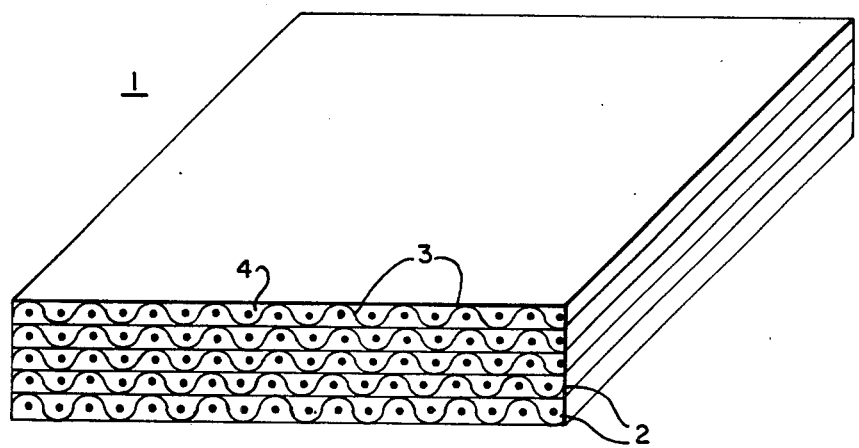

POLYIMIDE MODIFIED EPOXY RESINS IN AQUEOUS EMULSIONS FOR LAMINATION AND ELECTRODEPOSITION

BACKGROUND OF THE INVENTION

Until now the electrode deposition of polyimide-containing resins has been restricted to non-aqueous electrocoating systems that are low in resin solids. Because organic solvents are expensive, polluting, and possibly toxic, it would be highly desirable to be able to process polyimide containing resins by electrodeposition from an aqueous medium. The difficulty in doing this is that polyimides are generally not soluble in water. Thus, while it may be possible to electrodeposit polyamic acid resins from aqueous medium, and subsequently condense water from the resin to form the imide groups, until now it has not been possible to electrodeposit compounds that already contain an imide group from an aqueous medium.

SUMMARY OF THE INVENTION

We have discovered imide-containing compounds that can be rendered soluble in water, and have further found that these compounds attach themselves to the epoxy resin-containing droplets in an epoxy resin emulsion. When an emulsion is formed of the epoxy resin, a crosslinking agent, and the imide compound, all three compounds are electrodeposited together. Since the imide compound contains at least one group that is reactive with the epoxy resin, an epoxy-imide polymeric coating can be formed on the substrate when the electrodeposited compounds are heated and cured. If the substrate is, for example, graphite cloth, the resins deposited on the cloth can be partially cured to form a graphite prepreg which can be molded into a laminate. The resulting laminate is expected to have superior mechanical properties because we believe that the process of this invention promotes better adhesion between the fibers and the resin.

We have also found that the useful concentration of resin in the aqueous emulsion system of this invention is nearly 50%, which is more than 50 times greater than the concentration generally used in non-aqueous electrocoating processes. The process of this invention has the further advantage that it can be used either as an anodic electrodeposition process or cathodic electrodeposition process. In addition, of course, the elimination of organic solvents makes the process of this invention less expensive, nonpolluting, and less toxic.

DESCRIPTION OF THE INVENTION

The accompanying drawing is an isometric view in section of a certain presently preferred embodiment of a laminate prepared according to the process of this invention.

In the drawings, a laminate 1 consists of a number of prepregs 2, each of which is composed of woven cloth 3 impregnated with an electrodeposited resin 4.

In the first step of the process of this invention, a water soluble imide compound is prepared. The imide compound contains at least one imide group and is preferably aromatic, as aromatic groups enhance the thermal properties of resulting polymer. The imide compound must also contain at least one free carboxyl group in order to make it water soluble. Another way of stating this is that it should have an acid number of at least 60 milligrams KOH per gram of imide compound in order for it to be water soluble. The imide compound should be di- or multifunctional in groups, such as carboxyl or hydroxyl groups, that crosslink with epoxide groups, because if it is nonfunctional or monofunctional in those groups the resin will tend to be thermoplastic and may not gel. If the imide compound is di- or multifunctional, the crosslinked polymer will be epoxy terminated and can be crosslinked through the epoxy groups. If the imide compound is multifunctional, the additional functionality can be used to crosslink the resulting polymer and an epoxy crosslinking agent is not required.

The imide compound can be formed by the reaction of an anhydride, or a compound having vicinal carboxylic acid groups, with a primary amine. Suitable compounds include trimellitic anhydride, trimellitic acid, 3,3',4,4'-benzophenone tetracarboxylic dianhydride, pyromellitic dianhydride, tetrahydrofuran tetracarboxylic dianhydride, polyazelaic polyanhydride, 2,3,6-naphthalene tricarboxylic-2,3-monoanhydride, and maleinized vegetable oils, maleinized polybutadienes, and laser polymerized maleic anhydride oligomeric homopolymers. Suitable primary amines include m-phenylene diamine, methylene diamine, methylene diamylamine, diamyl diphenyl ether, diaminobenzanilide, and p-amino phenol. The anhydride and the primary amine are preferably reacted in stoichiometric proportions to form the imide compound. The preferred reactants are trimellitic anhydride (TMA) and p-amino phenol as they have been found to work well; their product is 4-p-hydroxphenyltrimellitimide (4-HPT):

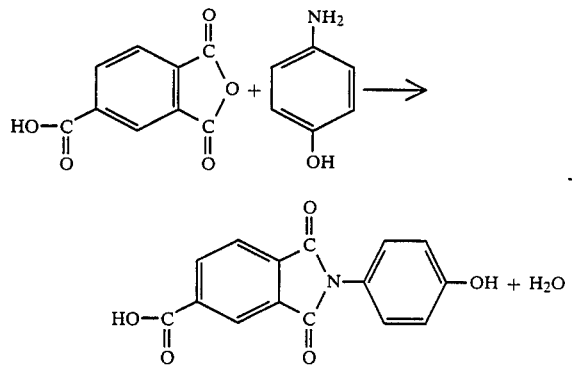

A solvent, such as dimethyl formamide (DMF), dimethyl acetamide (DMAC), dimethyl sulfoxide (DMSO), or N-methyl pyrroiidone (NMP), is used to dissolve the reactants; DMF is the preferred solvent because of cost and ease of handling. A suitable solids content for this reaction is about 25 to about 80% by weight.

The imide compound is made water soluble by neutralization of the free carboxyl group. Neutralization can be accomplished by adding the imide compound to a basic aqueous solution in the presence of a catalyst. While a basic aqueous solution can be formed by the addition of a strong base, such as sodium hydroxide, potassium hydroxide, or lithium hydroxide, to water, strong bases are not preferred as the resulting high pH may hydrolize the epoxy groups when the epoxy resin is added later. Preferably, the basic solution is formed using a water soluble amine. The amine should be water soluble because if it is not water soluble the amine salt of the imide compound will probably not be water soluble either. The water soluble amine should contain at least one tertiary nitrogen group in order to form the salt, and it should not contain any primary or secondary nitrogens as these will react with the carboxyl group and form an amic acid linkage between the imide compound and the amine. Sufficient water soluble amine should be used to make the imide compound water soluble. A solution of the amine is formed and the solid imide compound is added to the solution. If the imide compound does not dissolve completely, additional amine is added until the imide compound is in solution. The neutralization of 4-HPT with triethylamine, for example, is given by the following equation:

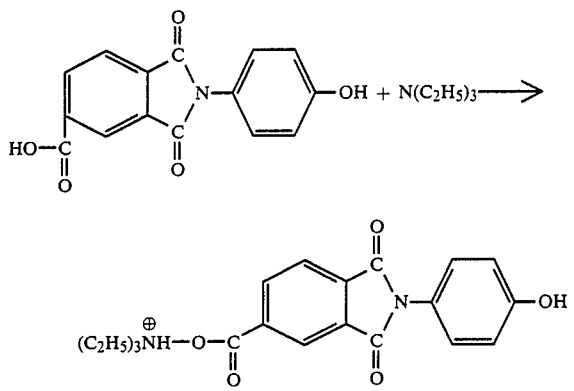

In the next step in the process of this invention, an emulsion is formed from the imide compound, water, and an epoxy resin. The epoxy resin is a water dispersed epoxy resin or a water emulsified epoxy resin, and the epoxy resin itself is not soluble in water. Water dispersed epoxy resins are preferred as they are more electrocoatable. Water dispersed and water emulsified epoxy resins can be made, but they are also commercially available products. They are sold with a small amount (up to about 15% by weight based on epoxy resin weight) of a water dispersible organic solvent such as butanol, methyl cellosolve, pentoxone, or methyl isobutyl ketone, to make the epoxy resin more compatible with water. In addition, the water dispersed epoxy resin or water emulsified epoxy resin can also contain about 1 to about 15 percent by weight (based on epoxy resin weight) of an emulsifying agent. The epoxy resin must be di- or multifunctional in epoxide groups or it will not chain extend. That is, monofunctional epoxies are unsuitable because they will not crosslink or gel. The epoxy resin is preferably aromatic because aromaticity enhances the thermal properties of the resulting polymer. The epoxy resin may be of any type, including novolac epoxies, diglycidyl ethers of bisphenol A, hydantoin epoxies, high performance multifunctional epoxies, diglycidyl ethers of bisphenol S, and other types of epoxy resins.

If the imide compound is not multifunctional, it is necessary that the emulsion also contain a crosslinking agent. Suitable crosslinking agents are well known in the art and include dicyandiamide, trimellitic acid, water soluble multi-carboxyl polyesters, and diphenolic acid. The crosslinking agent must be water compatible, which means that it must be water dispersible, water soluble, or water emulsifiable. Sufficient crosslinking agents should be present to fully cure the resin. Preferably, about 1 to about 15 equivalent percent of crosslinking agent is present, based on the equivalents of reactive epoxide groups which are present.

The emulsion is formed by mixing the solubilized imide with the water dispersed or water emulsified epoxy resin. The emulsion forms almost immediately when the solution of the imide compound and the epoxy dispersion or epoxy emulsion are mixed together, and no heat is required to form the emulsion. The emulsion consists of a discontinuous phase of droplets of epoxy resin to which adhere the imide compound and the crosslinking agent, and a continuous phase of water. The emulsion generally contains about 5 to about 60% solids. The proportion of imide compound to epoxy resin should be selected so that excess epoxy functionality is present, for otherwise it may be difficult to gel the resin. It is preferable to have about 1.5 to about 2.5 free epoxide groups per epoxide reactive functionality on the imide compound.

Electrodeposition can be accomplished in a conventional manner at room temperature using about 1 to about 500 volts DC on any conducting material including metals, carbon, or graphite. The substrate can be a flat sheet or can have any other shape including wires, mats, roving, or woven material. Woven graphite is preferred as it is useful in making high performance laminates. Whether the substrate is the anode or the cathode depends upon the particular epoxy resin being used, but generally the substrate will be the anode and an electrode immersed in the emulsion will be the cathode.

Instead of electrodeposition, the emulsion can also be sprayed onto conducting or non-conducting substrates, or various articles can be dipped into the emulsion. Fillers, pigments, and other additives that cannot be electrocoated can then be added to the emulsion. After the emulsion has been applied to the substrate by electrocoating or by other process, the resins in the emulsion are cured and crosslinked. This can generally be accomplished by heating at 150° to about 200° C. for at least one hour, which evaporates any water that is present and crosslinks the resins. A laminate can be prepared by B-staging the resin on the substrate to form a prepreg, stacking plys of prepregs, and heating under pressure to cure the resin to the C-stage. While the imide compound and the epoxy resin are electrodeposited as separate compounds, they react together when the resin is cured. The reaction, for example, of a diepoxide with 4-HPT is as follows:

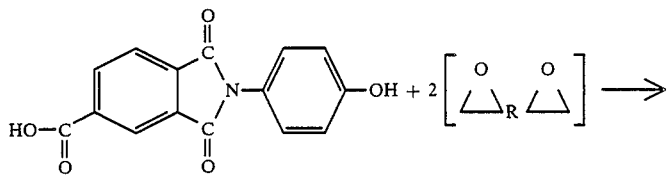

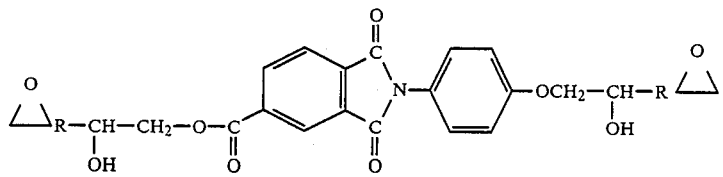

The following examples further illustrate this invention.

EXAMPLE 1

A 3,000 ml round bottom, three-necked flask fitted with an agitator, nitrogen inlet tube, thermometer, reflux condenser, and a means for heating was charged with 400.0 gm DMF. The flask was swept with $N_2$ gas for 5 minutes and the $N_2$ flow rate was adjusted to maintain a slight positive $N_2$ pressure in the flask throughout the balance of the run. The agitator was started and neat TMA (350.0 gm, 1.82 mole) was added to the DMF at such a rate as to prevent clumping. After addition of the TMA was completed, the slurry was slowly heated to 70° C. to effect complete TMA dissolution. After the TMA had dissolved, and with the reaction temperature at 70° C., p-aminophenol (196.4 gm, 1.80 mole) in powder form was charged to the reactor. After attaining an exotherm peak temperature of 107° C., the reaction mixture cooled to 90° C., amic acid formation was complete.

At this point in the procedure, a Dean-Stark distillation trap was placed between the flask and the condenser. Imidization was effected by heating the flask from 90° C. to 150° C. over a 35-minute period. At 150° C., approximately 39.0 gm of distillate was collected. The collected distillate was poured into an equal volume of toluene. After phase separation, the bottom layer contained about 34 ml of water. After distillate was no longer collected at 150° C., the flask was heated to 160° C. while continually removing DMF to insure complete imidization.

After 150 gm of DMF had been stripped from the reactor, the reaction mixture was cooled to 140° C. and poured into an ice-water mixture (900 gm of ice+900 gm of water) with vigorous stirring to precipitate the product. The lemon yellow precipitate was vacuum-filtered from the water, washed with methanol, dried 8 hours at 180° C. and 8 hours in vacuo at 110° C. to produce about 841 gm (yield≃92%) of dry, free-flowing, pale yellow 4-HPT.

A Perkin-Elmer Elemental Analyzer Model 240C was utilized to determine total carbon, hydrogen, and nitrogen. Oxygen was determined by difference. The results are given in the following table:

| Element | Calculated Wt. % | Found Wt. %* |
|---|---|---|
| Carbon | 63.58 | 63.89 |
| Hydrogen | 3.21 | 3.21 |
| Nitrogen | 4.95 | 5.04 |
| Oxygen | 28.26 | 27.86 |
| | 100.00 | 100.00 |

*Average of two determinations

An infrared scan of the 4-HPT was also performed. Bands at 1,770, 1,720, 1,380, and 720 $cm^{-1}$ indicated imide functionality.

Differential scanning calorimetry (DSC)/thermogravimetric analysis (TGA) was also done on the 4-HPT. The DSC scan showed a very sharp transition signifying a major thermal event which occurred at about 325° C. and corresponds to the melting point of the 4-HPT.

Programmed weight loss data via TGA ($N_2$) showed that the product retained stability to nearly 350° C. Beyond 325° C., there was a sharp increase in weight loss with about 50% retention in weight at 500° C. It is evident from this data that decomposition occurs at the melting point of the 4-HPT.

The water soluble, triethylamine salt of the 4-HPT product of Example 1 was prepared by charging 124.5 gm of de-ionized water into a stainless steel beaker fitted with a propeller-type, air-driven agitator. With the agitator running at slow speed, triethylamine (16.0 gm, 0.159 equivalent) was charged to the beaker followed by the slow addition of the 4-HPT (45.0 gm, 0.159 equivalent). Solubilization occurred upon addition of the 4-HPT and resulted in a transparent amber colored solution. The clear amber solution was stirred at medium speed and 2-methylmidazole catalyst (0.8 gm) was charged followed by the addition of dicyandiamide (3.6 gm, 0.173 equivalent). The solution was stirred until the added components dissolved.

EXAMPLE 2

A water-based laminating varnish was formulated to contain 15.0% excess epoxide (equivalent basis) by charging 417.0 gm (0.391 equivalent) of a water dispersion of a diglycidyl ether bisphenol A (0.391 equivalent and 79.28 weight percent non-volatile content) sold by Celanese Corporation as "CMD-35201," into a beaker fitted with an air-driven propeller agitator. With the agitator set at medium speed, the solubilized 4-HPT salt solution made in Example 1 (containing predissolved dicyandiamide and 2-methylimidazole) was slowly added to the "CMD 35201." The resulting solution was stirred 15 minutes prior to impregnation. No varnish coagulation was observed prior to or during impregnation with the varnish. Varnish properties are presented in the following table.

| | |
|---|---|
| Set-Time, Minutes | 13.9 |
| Viscosity, cps | 27.5* |
| Solids, Content, Wt. % | 50.0 |

*Spindle #1 @ 20 rpm, Model LVF.

Style 7628 fiberglass cloth was utilized to prepare 15"×15" prepregs from the varnish. The varnish impregnated substrates were B-staged to form prepregs by placing them in an oven at 150° C. for 5 minutes. Additional varnish was placed on the prepregs to raise the resin content to 47.8% resin. Second pass B-staging conditions were 4 minutes at 150° C. The double impregnation step was necessitated by usual difficulties encountered during hand impregnation of water-based laminating varnishes. (Note that the triethylamine utilized to solubilize the emulsion is lost during B-staging.)

The double-passed, B-staged prepregs were cut into 7"×7" squares and press laminated by stacking nine individual pieces between steel caul plates with Tedlar mold release sheets between the caul plates and the prepreg stack. The molding pack was placed into a cold press and heated to 170° C. under 500 psi with an hour hold between 170°–180° C. Cooldown was done under pressure.

Programmed weight loss data in flowing $N_2$ via thermogravimetric analysis showed ~90% weight retention at 400° C. and an apparent Tg of ~135° C.

Two aluminum panels (1"×6"×0.06") were used as the anode and the cathode, and were placed in the emulsion of Example 1 two inches deep and one inch apart. Electrodeposition was carried out at 100 mA until the current charge was nearly zero (about a two minute duration). The coated anode was removed from the bath and was washed with a stream of water. The adhesion of the coated film to the aluminum was good as shown by excellent resistance of the coating to being washed off by the water stream. Thumbnail pressure was required to separate the resin from the coated piece. The film after removal from the bath was dry to the touch and was not sticky. The coated electrode was heated at 180° C. for 15 minutes to cure the film. The coating was flexible and did not crack when the coated piece was twisted or bent by manual manipulation. The coating withstood creasing without cracking. The electrical breakdown was on the order of 2600 to 3000 volts AC per mil of cured film thickness. The electrodeposited coatings were approximately 1.5 mils thick. The throwing power of the resin was good.

The same emulsion was used to electrocoat three pieces of graphite cloth (2"×2"). The electrocoating was carried out as before using the graphite cloth as the anode. The coated pieces were allowed to air dry for 16 hours or were B-staged at 150° C. to 3 minutes. They were then pressed at 1000 psi for 30 minutes at 180° C. using Teflon films as release sheets. The resultant laminates were structurally sound and had good appearance and composite integrity. The adhesion between plys of graphite was excellent.

What we claim is:

1. An emulsion made by the process of mixing:
   (1) an epoxy resin composition selected from the group consisting of water dispersed epoxy resin and water emulsified epoxy resin, where the epoxy resin has at least two epoxide groups and itself is not soluble in water;
   (2) a solution of a water soluble salt of a di or multifunctional imide compound, which imide compound contains at least one imide group and at least one free carboxyl group; and
   (3) when the imide compound is non-multifunctional, a water compatible crosslinking agent.

2. An emulsion according to claim 1 wherein the equivalent ratio of reactive epoxide functionality on the epoxy resin, to the functional groups on the imide compound that are reactive therewith, is about 1.5 to about 2.5.

3. An emulsion according to claim 1 wherein said imide compound is aromatic.

4. An emulsion according to claim 1 wherein said imide compound has an acid number of at least 60 mg KOH per gram.

5. An emulsion according to claim 1 wherein said imide compound is the reaction product of an anhydride, or a compound having vicinal carboxylic acid groups, and a primary amine.

6. An emulsion according to claim 5 wherein said anhydride or compound having vicinal carboxylic acid groups is selected from the group consisting of trimellitic anhydride, trimellitic acid, 3,3',4,4'-benzophenone tetracarboxylic dianhydride, pyromellitic dianhydride, tetrahydrofuran tetracarboxylic dianhydride, polyazelaic polyanhydride, 2,3,6-napthalene tricarboxylic-2,3-monoanhydride, maleinized vegetable oils, maleinized polybutadienes, and laser polymerized maleic anhydride oligomeric homopolymers.

7. An emulsion according to claim 5 wherein said primary amine is selected from the groups consisting of m-phenylene diamine, methylene diamine, methylene diamylamine, diamyl diphenyl ether, diaminobenzanilide, and p-amino phenol.

8. An emulsion according to claim 1 wherein said epoxy resin is selected from the group consisting of novolac epoxies, diglycidyl ethers of bisphenol A, hydantoin epoxies, high performance multifunctional epoxies, and diglycidyl ethers of bisphenol S.

9. An emulsion according to claim 1 wherein said crosslinking agent is selected from the group consisting of dicyandiamide, trimellitic acid, water soluble multicarboxyl polyesters, and diphenolic acid.

10. An emulsion made by the process of mixing:
    (1) an aromatic epoxy resin composition selected from the group consisting of water dispersed epoxy resin and water emulsified epoxy resin, where the epoxy resin has at least two epoxide groups;
    (2) a solution of a water soluble tertiary amine salt of an aromatic imide having at least one imide group, and at least two groups that are reactive with said epoxide groups, at least one of which is a carboxyl group, where the equivalent ratio of reactive epoxide functionality on said epoxy resin to said functional groups on said aromatic imide that are reactive therewith is about 1.5 to about 2.5; and
    (3) a water compatible crosslinking agent,
    said emulsion having a solids content of about 5% to about 60% by weight, based on total emulsion weight.

11. An emulsion according to claim 10 wherein said epoxy resin includes about 1 to about 15% by weight, based on epoxy resin weight, of an emulsifying agent, and up to about 15% by weight, based on epoxy resin weight, of a water-dispersible organic solvent.

* * * * *